(12) United States Patent
Casara et al.

(10) Patent No.: US 7,576,120 B2
(45) Date of Patent: Aug. 18, 2009

(54) AZABICYCLIC COMPOUNDS, A PROCESS FOR THEIR PREPARATION AND PHARMACEUTICAL COMPOSITIONS CONTAINING THEM

(75) Inventors: Patrick Casara, Vilennes sur Seine (FR); Anne-Marie Chollet, Le Pecq (FR); Alain Dhainaut, Chatou (FR); Lionel Bert, Marly le Roi (FR); Pierre Lestage, La Celle Saint Cloud (FR); Brian Lockhart, Feucherolles (FR)

(73) Assignee: Les Laboratoires Servier, Suresnes Cedex (FR)

( * ) Notice: Subject to any disclaimer, the term of this patent is extended or adjusted under 35 U.S.C. 154(b) by 188 days.

(21) Appl. No.: 10/589,831

(22) PCT Filed: Feb. 20, 2005

(86) PCT No.: PCT/FR2005/000382

§ 371 (c)(1),
(2), (4) Date: Aug. 17, 2006

(87) PCT Pub. No.: WO2005/089747

PCT Pub. Date: Sep. 29, 2005

(65) Prior Publication Data

US 2007/0197625 A1     Aug. 23, 2007

(30) Foreign Application Priority Data

Feb. 20, 2004   (FR) .................................. 04 01690

(51) Int. Cl.
*A61K 31/40* (2006.01)
*C07D 209/44* (2006.01)
(52) U.S. Cl. ...................................... 514/412; 548/515
(58) Field of Classification Search ................ 548/515; 514/412
See application file for complete search history.

(56) References Cited

U.S. PATENT DOCUMENTS 5,703,091 A    12/1997  Munschauer et al.
7,034,182 B2 *  4/2006  Fang et al. .................. 564/147

FOREIGN PATENT DOCUMENTS

WO         02/06223       1/2002

OTHER PUBLICATIONS

Svendsen et al., 1988, CAS: 109:210691.*

International Preliminary Report on Patentability for PCT/FR2005/000382 of Nov. 1, 2006.
Faghih, et al., "Aminoalkoxybiphenylnitriles as Histamine-3 Receptor Ligands" Bioorganic and Medicinal Chemistry Letters, vol. 112, pp. 3077-3079, 2002.
International Search Report for PCT/FR2005/000382 of Jul. 7, 2005.
Witkin, et al., *Pharmacology and Therapeutics*, 2004, 103, 1-20.
Leurs, et al., *TiPS*, 1998, vol. 19, 177-183.
Arrang, et al., *Nature*, 1983, 302, 832-837.
Leurs, et al., *Nature Reviews/Drug Discovery*, 2005, vol. 4, 107-120.
Passani, et al., *European Journal of Neuroscience*, 2001, 14, 1522-1532.
Prast, et al., *Brain Research*, 1996, 734, 316-318.
Ligneau, et al., *J. Pharm. Exper. Ther.*, 1998, 287, 658-666.
Fox, et al., *Behav. Brain Res.*, 2002, 131, 151-161.
Fox, et al., *J. Pharm. Exper. Ther.*, 2003, 305, 897-908.
Meguro, et al., *Pharmacology Biochemistry and Behavior*, 1995, 50, 321-325.
Giovannini, et al., *Behav. Brain Res.*, 1999, 104, 147-155.
Stark, et al., *Arch. Pharm. Pharm. Med. Chem.*, 1998, 331, 211-218.
Onodera, et al., *Naunyn-Schmiedeberg's Arch Pharmacol*, 1998, 357, 508-513.
Bacciottini, et al., *Behav. Brain Res.*, 2001, 124, 183-194.

* cited by examiner

*Primary Examiner*—Rei-tsang Shiao
(74) *Attorney, Agent, or Firm*—Hueschen and Sage

(57) ABSTRACT

A compound selected from those of formula (I):

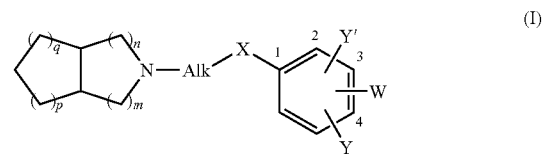

wherein
  m and n, which may be identical or different, each represent an integer from 0 to 2 inclusive, with the sum of the two integers being from 2 to 3 inclusive,
  p and q, which may be identical or different, each represent an integer from 0 to 2 inclusive,
  Alk represents an alkylene, alkenylene or alkynylene chain,
  X represents an oxygen atom, a sulphur atom or an —N(R)— group wherein R represents a hydrogen atom or an alkyl group,
  Y, Y' and W are as defined in the description, its enantiomers, diastereoisomers, and addition salts thereof with one or more pharmaceutically acceptable acid or base.

Medicinal products containing the same which are useful for treating conditions associated with central histaminergic systems.

30 Claims, No Drawings

AZABICYCLIC COMPOUNDS, A PROCESS FOR THEIR PREPARATION AND PHARMACEUTICAL COMPOSITIONS CONTAINING THEM

The present invention relates to new azabicyclic compounds, to a process for their preparation and to pharmaceutical compositions containing them.

The compounds of the present invention are of particular interest from a pharmacological point of view for their interaction with the central histaminergic systems in vivo, and may be used in the treatment of neuropathologies associated with cerebral ageing, mood disorders, eating behaviour disorders and sleep/wake cycle disturbances, as well as attention deficit hyperactivity syndrome.

Ageing of the population as a result of the increase in life expectancy at birth has in parallel brought about a substantial increase in the incidence of neuropathologies associated with age, and especially Alzheimer's disease. The principal clinical manifestations of cerebral ageing and especially neuropathologies associated with age are mnesic and cognitive function deficiencies, which may lead to dementia.

In respect of the central nervous system, recent neuropharmacological studies have demonstrated that histamine, via the central histaminergic systems, plays the role of a neurotransmitter or neuromodulator in physiological or pathophysiological settings (Pell and Green, *Annu. Rev. Neurosci.,* 1986, 9, 209-254; Schwartz et al., *Physiol. Rev.,* 1991, 71, 1-51). Thus, it has been demonstrated that histamine plays a part in various physiological and behavioural processes such as thermoregulation, neuroendocrine regulation, circadian rhythm, cataleptic states, motor function, aggressiveness, eating behaviour, learning and memory function, and also synaptic plasticity (Hass et al., *Histaminergic neurones: morphology and function,* Boca Raton, Fla.: CRC Press, 1991, pp. 196-208; Brown et al., *Prog. Neurobiology,* 2001, 63, 637-672).

Studies carried out in animals have demonstrated that an increase in endogenous extra-synaptic levels of histamine enables the promotion of states of alertness, the promotion of learning and memory processes and the regulation of food intake and enables convulsive attacks to be countered. (Brown et al., *Prog Neurobiol.,* 2000, 63, 637-672; Passani et al., *Neurosci. Biobehav. Rev.,* 2000, 24, 107-113). As a result, potential therapeutic indications for compounds capable of increasing the turnover or release of histamine centrally are the treatment of cognitive deficiencies associated with cerebral ageing and with neurodegenerative diseases, such as Alzheimer's disease, Pick's disease, Korsakoff's disease and frontal lobe or sub-cortical dementias of vascular or other origins, as well as the treatment of mood disorders, convulsive attacks and attention deficit hyperactivity syndrome. Furthermore, works have shown that a histamine injection at the level of the central hypothalamic nuclei involved in the regulation of satiety reduces feeding in the rat. In addition, a hypofunctioning of histaminergic transmission has been demonstrated in genetically obese rats (Machidori et al., *Brain Research,* 1992, 590, 180-186). As a result, eating behaviour disorders and obesity are likewise potential therapeutic indications for the compounds of the present invention.

A number of documents describe compounds comprising an octahydrocyclopenta-[b]pyrrole or octahydrocyclopenta [c]pyrrole moiety [U.S. Pat. No. 2,962,496; *J. Chem. Soc., Chem. Commun.,* 1995, 10, 1009-1010; *Tetrahedron,* 1991, 47(28), 5161-5172; *Tetrahedron Lett.,* 1988, 29 (28), 3481-3482; *J. Med. Chem.,* 1973, 16(4), 394-397]. Some of those compounds are known for their use in the treatment of cardiovascular diseases, especially hypertension, or as a local anaesthetic, and others have been studied from the point of view of mechanism in relation to chemical reactions of the catalysed intramolecular cyclisation or cycloaddition type. On the other hand, there is no document that either describes or suggests for those compounds an in vivo activity as activators of the central histaminergic systems, a novel property of the compounds claimed by the Applicant.

More especially, the present invention relates to the compounds of formula (I):

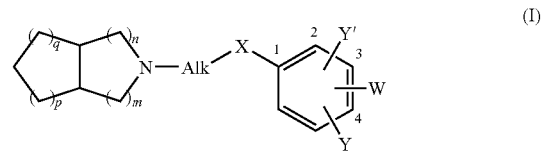

wherein:
  m and n, which may be identical or different, each represent an integer of from 0 to 2 inclusive, with the sum of the two integers being from 2 to 3 inclusive,
  p and q, which may be identical or different, each represent an integer of from 0 to 2 inclusive,
  Alk represents an alkylene, alkenylene or alkynylene chain,
  Y and Y', which may be identical or different, each represent a hydrogen atom, a halogen atom or an alkyl, alkoxy, alkylthio, alkylsulphinyl, alkylsulphonyl, mercapto, hydroxy, perhaloalkyl, nitro, amino (unsubstituted or substituted by one or two alkyl groups), acyl, aminocarbonyl (optionally substituted on the nitrogen atom by one or two alkyl groups), acylamino (optionally substituted on the nitrogen atom by an alkyl group), alkoxycarbonyl, carboxy, sulpho or cyano group,
  X represents an oxygen atom, a sulphur atom or an —N(R)— group wherein R represents a hydrogen atom or an alkyl group,
  W represents a group selected from cyano (when X represents an oxygen atom or an —N(R)— group), —N($R_1$)-$Z_1$-$R_2$ and -$Z_2$-N$R_1R_2$,
  wherein:
    $Z_1$ represents —C(O)—, —C(S), —C(N$R_4$)—, *—C(O)—N($R_3$)—, *—C(S)—N($R_3$)—, *—C(N$R_4$)—N($R_3$)—, *—C(O)O—, *—C(S)—O— or —S(O)$_r$—, in which r=1 or 2 and * corresponds to the point of attachment to N($R_1$),
    $Z_2$ represents —C(O)—, —C(S)—, —C(N$R_4$)—, —S(O)$_r$— or a bond,
    $R_1$, $R_2$, $R_3$ and $R_4$, which may be identical or different, each represent a hydrogen atom, an optionally substituted alkyl group, optionally substituted alkenyl group, optionally substituted alkynyl group, alkoxy group, optionally substituted cycloalkyl group, optionally substituted heterocycloalkyl group, optionally substituted aryl group or optionally substituted heteroaryl group,
    or $R_1$ and $R_2$ or $R_2$ and $R_3$, together with the atom or atoms carrying them, form an optionally substituted heterocycloalkyl or optionally substituted heteroaryl group, to their enantiomers, diastereoisomers, and also addition salts thereof with one or more pharmaceutically acceptable acids or one or more pharmaceutically acceptable bases, wherein:
the term "alkyl" denotes a linear or branched hydrocarbon chain containing from 1 to 6 carbon atoms,
the term "alkenyl" denotes a linear or branched group containing from 3 to 6 carbon atoms and from 1 to 3 double bonds,
the term "alkynyl" denotes a linear or branched group containing from 3 to 6 carbon atoms and from 1 to 3 triple bonds,
the term "alkoxy" denotes an alkyl-oxy group in which the linear or branched alkyl chain contains from 1 to 6 carbon atoms,
the expression "optionally substituted aryloxy" denotes an aryl-oxy group in which the aryl group is optionally substituted,
the term "acyl" denotes an $R_aC(O)$— group in which $R_a$ represents a hydrogen atom or an alkyl group,
the term "perhaloalkyl" denotes a linear or branched carbon chain containing from 1 to 3 carbon atoms and from 1 to 7 halogen atoms,
the term "alkylene" denotes a linear or branched bivalent radical containing from 1 to 6 carbon atoms,
the term "alkenylene" denotes a linear or branched bivalent radical containing from 2 to 6 carbon atoms and from 1 to 3 double bonds,
the term "alkynylene" denotes a linear or branched bivalent radical containing from 2 to 6 carbon atoms and from 1 to 3 triple bonds,
the term "aryl" denotes a phenyl, naphthyl, indanyl, indenyl, dihydronaphthyl or tetrahydronaphthyl group,
the term "heteroaryl" denotes a monocyclic or bicyclic group in which at least one of the rings is aromatic, the group containing from 5 to 11 ring members and from 1 to 4 hetero atoms selected from nitrogen, oxygen and sulphur,
the term "cycloalkyl" denotes a hydrocarbon monocycle or bicycle containing from 3 to 11 carbon atoms and optionally unsaturated by 1 or 2 unsaturated bonds,
the term "heterocycloalkyl" denotes a mono- or bi-cyclic group, saturated or unsaturated by 1 or 2 unsaturated bonds, the group containing from 4 to 11 ring members and having from 1 to 4 hetero atoms selected from nitrogen, oxygen and sulphur,
the expression "optionally substituted" applied to the terms cycloalkyl, aryl, heteroaryl and heterocycloalkyl denotes either i) that those groups may be substituted by from 1 to 3 identical or different substitutents selected from alkyl, alkoxy, alkylthio, alkylsulphinyl, alkylsulphonyl, halogen, hydroxy, mercapto, perhaloalkyl, nitro, amino (unsubstituted or substituted by one or two alkyl groups), acyl, aminocarbonyl (optionally substituted on the nitrogen atom by one or two alkyl groups), acylamino (optionally substituted on the nitrogen atom by an alkyl group), alkoxycarbonyl, carboxy, sulpho and cyano, or ii) that those groups may be substituted by an aryl, heteroaryl, cycloalkyl, heterocycloalkyl or benzyl group; it being understood that the aryl or heteroaryl groups may in addition be substituted by one or two oxo groups on the non-aromatic moiety of the groups containing an aromatic moiety and a non-aromatic moiety and that the cycloalkyl or heterocycloalkyl groups may be substituted likewise by one or two oxo groups,
the expression "optionally substituted" applied to the term alkyl, alkenyl or alkynyl denotes that those groups may be substituted by one or two identical or different groups selected from alkylthio, alkylsulphinyl, alkylsulphonyl, alkoxy, halogen, hydroxy, mercapto, nitro, amino, acyl, aminocarbonyl, acylamino, alkoxycarbonyl, carboxy, sulpho, cyano, optionally substituted aryl, optionally substituted heteroaryl, optionally substituted cycloalkyl, optionally substituted heterocycloalkyl and optionally substituted aryloxy.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, oxalic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned, without implying any limitation, sodium hydroxide, potassium hydroxide, triethylamine etc.

Preferred aryl groups are the phenyl group.

Advantageously, the compounds of the invention are those wherein, in formula (I), q is 1.

An advantageous embodiment of the invention relates to compounds wherein n represents 1.

Preferred compounds of the invention are those wherein m is 1.

Other preferred compounds of the invention are those wherein m is 2.

Preferred compounds of the invention are those wherein p is 1.

Other preferred compounds of the invention are those wherein p is 2.

An especially advantageous embodiment of the invention relates to compounds of formula (I) wherein X represents an oxygen atom or a sulphur atom (more advantageously an oxygen atom).

Another especially advantageous embodiment of the invention relates to compounds of formula (I) wherein X represents an —N(R)— group (more advantageously NH).

A preferred embodiment is that in which the groups Y and Y' in the compounds of the invention of formula (I) each represent a hydrogen atom.

Another preferred embodiment of the invention is that in which, in the compounds of the invention of formula (I), the group Y represents a hydrogen atom and the group Y' represents a halogen atom or an alkyl, alkoxy, alkylthio, alkylsulphinyl, alkylsulphonyl, mercapto, hydroxy, perhaloalkyl, nitro, amino (unsubstituted or substituted by one or two alkyl groups), acyl, aminocarbonyl (optionally substituted on the nitrogen atom by one or two alkyl groups), acylamino (optionally substituted on the nitrogen atom by an alkyl group), alkoxycarbonyl, carboxy, sulpho or cyano group. More preferably, Y' represents a halogen atom.

Especially advantageous compounds include the compounds of the invention wherein Alk represents an alkylene chain (more especially propylene).

An especially advantageous embodiment of the invention relates to compounds of formula (I) wherein W is located on the phenyl group in the 4-position.

Another advantageous embodiment of the invention relates to compounds of formula (I) wherein W represents a cyano group.

Advantageously, the compounds of formula (I) are those wherein W represents an —N($R_1$)-$Z_1$-$R_2$ group.

Also advantageously, the compounds of formula (I) are those comprising W representing a -$Z_2$-N$R_1R_2$ group.

Preferred $Z_2$ groups are selected from —C(O)—, —C(S)—, —C(N$R_4$)— and —S(O)$_r$—. More preferably, $Z_2$ represents a —C(O)— group.

Other preferred compounds of the invention are those wherein $Z_2$ represents a bond.

Preferred $Z_1$ groups are selected from —C(O)—, —C(S)—, *—C(O)—N($R_3$)—, *—C(S)—N($R_3$)—, *—C(O)—O— and —S(O)$_2$—, preferably —C(O)— and *—C(O)—N($R_3$)— (more preferably —C(O)—).

An especially advantageous embodiment of the invention relates to compounds of formula (I) wherein $R_1$, $R_2$, $R_3$ and $R_4$, which may be identical or different, each represent:
- a hydrogen atom;
- an alkoxy group;
- a cycloalkyl group (preferably cyclopropyl, cyclobutyl or cyclohexyl);
- a phenyl group that is optionally substituted (preferably by one or two substitutents selected from nitro, halogen, trihaloalkyl, alkyl and alkoxy);
- a naphthyl group;
- a heteroaryl group (preferably selected from thienyl, furyl, pyridyl, benzofuryl and methylenedioxyphenyl);
- an alkyl group;
- or an alkyl group substituted:
  - by a phenyl group that is optionally substituted (preferably by one or two substitutents selected from halogen, trihaloalkyl, alkyl and alkoxy),
  - or by a cycloalkyl (preferably cyclopropyl) group,
  - or by a heterocycloalkyl (preferably morpholinyl, piperazinyl, piperidinyl) group,
  - or by a heteroaryl (preferably thienyl, furyl, pyridyl, imidazolyl) group,
  - or by one or two alkoxy (preferably methoxy) groups, or by a phenyloxy group.

Another especially advantageous embodiment of the invention relates to compounds of formula (I) wherein W represents a group selected from —N($R_1$)—C(O)—N$R_2R_3$; —N($R_1$)—C(S)—N$R_2R_3$; —C(O)—N$R_1R_2$ and —C(S)—N$R_1R_2$; wherein $R_1$ and $R_2$ or $R_2$ and $R_3$, together with the atom or atoms carrying them, form a heterocycloalkyl group or a piperidinopiperidinyl group.

Preferred heterocycloalkyl groups are either saturated monocyclic groups having 6 or 7 ring members optionally containing, in addition to the nitrogen atom, another hetero atom selected from nitrogen, oxygen and sulphur; or saturated bicyclic groups having from 6 to 10 ring members optionally containing, in addition to the nitrogen atom, another hetero atom selected from nitrogen, oxygen and sulphur.

Another especially advantageous embodiment of the invention relates to compounds of formula (I) wherein W represents a -$Z_2$-N$R_1R_2$ group in which $Z_2$ represents a bond;

$R_1$ and $R_2$, together with the nitrogen atom carrying them, form a heteroaryl group (preferably imidazolyl or triazolyl) or $R_1$ represents a hydrogen atom or an alkyl group and $R_2$ represents an aryl or heteroaryl group (preferably heteroaryl, more preferably a group selected from quinazolyl, isoquinolyl, quinolyl and purinyl).

Advantageously, the compounds of formula (I) are those wherein W represents a —C(O)—N$R_1R_2$ group in which $R_1$ and $R_2$, together with the nitrogen atom carrying them, form a group selected from piperazinyl optionally substituted by an alkyl or benzyl group; piperidinyl optionally substituted by an alkyl or benzyl group; azepanyl; morpholinyl; thiomorpholinyl; octahydrocyclopentapyrrolyl; dihydroquinolinyl; and tetrahydroquinolinyl.

An especially advantageous embodiment of the invention relates to compounds of formula (I) wherein W represents a —C(O)—N$R_1R_2$ group in which $R_1$ and $R_2$, independently, each represent an alkyl group or a hydrogen atom.

Another especially advantageous embodiment of the invention relates to compounds of formula (I) wherein W represents a —N($R_1$)—C(O)—$R_2$ group in which $R_1$ and $R_2$, independently, each represent an alkyl group or a hydrogen atom.

Among the preferred compounds of the invention there may be mentioned, more especially, 4-(3-hexahydrocyclopenta[c]pyrrol-2(1H)-ylpropoxy)benzonitrile, 4-[(3-hexahydrocyclopenta[c]-pyrrol-2(1H)-ylpropoxy)benzamide, 4-[3-(hexahydrocyclopenta[c]-pyrrol-2(1H)-yl)propoxy]-N-methylbenzamide, 4-[3-(hexahydrocyclopenta[c]pyrrol-2(1H)-yl)propoxy]-N,N-dimethylbenzamide and N-[4-(3-hexahydrocyclopenta[c]pyrrol-2(1H)-yl)propoxy)phenyl]acetamide.

The invention relates also to a process for the preparation of compounds of formula (I), which is characterised in that there is used as starting material a compound of formula (II):

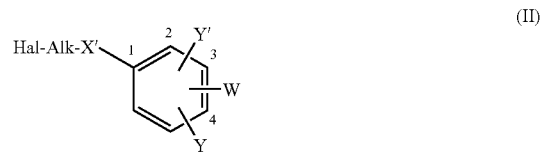

(II)

wherein:
Alk is as defined for formula (I), Hal represents a halogen atom, X' represents an oxygen atom, a sulphur atom or an —N(p)- group, in which (p) represents a hydrogen atom, a conventional protecting group for the nitrogen atom, or an alkyl group, and W, Y and Y' are as defined for formula (I), which compound of formula (II), after deprotection where appropriate, is condensed in basic medium with a bicycle of formula (III):

(III)

wherein:
n, m, p and q are as defined for formula (I), to yield a compound of formula (I), which compound of formula (I), when W represents a cyano group, is optionally reacted with sodium hydroxide or potassium hydroxide to yield a compound of formula (I/b):

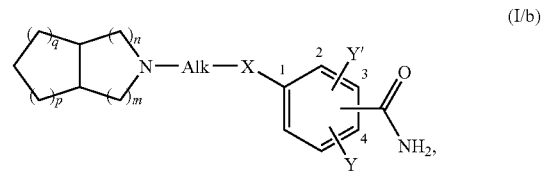

(I/b)

a particular case of the compounds of formula (I) wherein Alk, n, m, p, q, X, Y and Y' are as defined for formula (I), which compounds of formula (I), may, if necessary, be purified according to a conventional purification technique, are separated, where appropriate, into stereoisomers according to a conventional separation technique, are converted, if desired, into addition salts with one or more pharmaceutically acceptable acids or one or more pharmaceutically acceptable bases, it being understood that:

at any moment considered appropriate during the course of the process described above, the group or groups carbonyl, thiocarbonyl, amino, alkylamino of the starting reagent (II) can be protected and then, after condensation, deprotected, as required by the synthesis, the reagents (II) and (III) are prepared according to known procedures described in the literature.

The present invention relates also to pharmaceutical compositions comprising as active ingredient at least one compound of formula (I), alone or in combination with one or more pharmaceutically acceptable, inert, non-toxic excipients or carriers.

Among the pharmaceutical compositions according to the invention there may be mentioned, more especially, those which are suitable for oral, parenteral, nasal or transdermal administration, tablets or dragées, sublingual tablets, gelatin capsules, lozenges, suppositories, creams, ointments, dermal gels, etc.

The useful dosage varies in accordance with the age and weight of the patient, the nature and the severity of the disorder, and also the administration route, which may be oral, nasal, rectal or parenteral. Generally, the unit dosage ranges from 0.05 to 500 mg for a treatment of from 1 to 3 administrations per 24 hours.

The following Examples illustrate the invention and do not limit it in any way. The structures of the described compounds were confirmed by customary spectroscopic and spectrometric techniques.

The starting materials used are known products or products prepared according to known procedures.

Preparation 1: N-(4-Chlorobutyl)-N-(4-cyanophenyl)acetamide 9 g (54.1 mmol) of N-(4-cyanophenyl)acetamide are dissolved in 100 ml of THF. The mixture is cooled to 0° C. before the dropwise addition of 51 ml of a 1.6 N solution in hexane of nBuLi (1.5 eq.). The solution is left for one hour to return to ambient temperature and is then cooled to 0° C. before the dropwise addition of 9.9 ml of 1-chloro-4-iodobutane (81 mmol). The reaction mixture is stirred at ambient temperature for 18 h and then hydrolysed with a saturated aqueous solution of ammonium chloride (100 ml) and extracted with ethyl acetate. The organic phases are combined, dried over magnesium sulphate and concentrated. Purification by chromatography on silica (eluant: petroleum ether/ethyl acetate: 1/1) yields a yellow oil containing the expected product.

Preparation 2: N-(3-Chloropropyl)-N-(4-cyanophenyl)acetamide

The experimental procedure is identical to that of Preparation 1, with the replacement of 1-chloro-4-iodobutane with 1-chloro-3-iodopropane.

Preparation 3: N-(2-Chloroethyl)-N-(4-cyanophenyl)acetamide

The experimental procedure is identical to that of Preparation 1, with the replacement of 1-chloro-4-iodobutane with 1-chloro-2-iodoethane.

EXAMPLE 1

4-(3-Hexahydrocyclopenta[c]pyrrol-2(1H)-ylpropoxy)benzonitrile oxalate

Step 1: 4-(3-Chloropropoxy)benzonitrile

A mixture of 0.47 g (0.004 mol) of 4-hydroxybenzonitrile, 0.63 g (0.004 mol) of 1-bromo-3-chloropropane and 1.95 g (0.006 mol) of caesium carbonate in 10 ml of acetonitrile is heated at reflux for 5 hours.

Step 2: 4-(3-Hexahydrocyclopenta[c]pyrrol-2(1H)-ylpropoxy)benzonitrile oxalate

There are added to the reaction mixture of Step 1, at ambient temperature, 0.44 g (0.004 mol) of octahydrocyclopenta[c]pyrrole* and 0.30 g (0.002 mol) of sodium iodide and heating at reflux is resumed for 16 hours. The precipitate is filtered off and rinsed with acetonitrile. The filtrate is concentrated to dryness. The residue is taken up in dichloromethane. The resulting solution is extracted with sodium hydroxide solution, then with water, dried over magnesium sulphate and concentrated to dryness. The residue is purified by preparative chromatography technique on Lichroprep RP-18 phase. The title product is recrystallised from ethanol in oxalate form.

*The octahydrocyclopenta[c]pyrrole was synthesised according to the Roussi and Zang method (*Tetrahedron Lett.*, 1988, 29, 3481).

ESI$^+$: [M+H]$^+$ 271.1810 (theory: 271.1810)

EXAMPLE 2

4-(2-Hexahydrocyclopenta[c]pyrrol-2(1H)-ylethoxy)benzonitrile oxalate

The experimental procedure is identical to that of Example 1, with the replacement of 1-bromo-3-chloropropane in Step 1 with 1-bromo-2-chloroethane.

Elemental Microanalyses:

|  | C % | H % | N % |
|---|---|---|---|
| Calculated: | 62.42 | 6.40 | 8.09 |
| Found: | 62.09 | 6.38 | 8.09 |

EXAMPLE 3

4-(4-Hexahydrocyclopenta[c]pyrrol-2(1H)-ylbutoxy)benzonitrile oxalate

The experimental procedure is identical to that of Example 1, with the replacement of 1-bromo-3-chloropropane in Step 1 with 1-bromo-2-chlorobutane.

Elemental Microanalyses:

|  | C % | H % | N % |
|---|---|---|---|
| Calculated: | 63.28 | 6.89 | 7.31 |
| Found: | 63.14 | 6.78 | 6.91 |

EXAMPLE 4

N-[4-(3-Hexahydrocyclopenta[c]pyrrol-2(1H)-ylpropoxy)-phenyl]acetamide oxalate The experimental procedure is identical to that of Example 1, with the replacement of 4-hydroxybenzonitrile in Step 1 with N-(4-hydroxyphenyl)acetamide.

$^1$H NMR (DMSO D$_6$): δ (ppm): 1.40-1.80 (m,6H); 2.00 (s,3H); 2.10 (quint,2H); 2.80 (m,4H); 3.25 (t,2H); 3.60 (m,2H); 4.00 (t,2H); 6.90 (d,2H); 7.50 (d,2H); 9.80 (s, 1H).

EXAMPLE 5

N-[3-(3-Hexahydrocyclopenta[c]pyrrol-2(1H)-ylpropoxy)-phenyl]acetamide oxalate The experimental procedure is identical to that of Example 1, with the replacement of 4-hydroxybenzonitrile in Step 1 with N-(3-hydroxyphenyl)acetamide.

Elemental Microanalyses:

|  | C % | H % | N % |
|---|---|---|---|
| Calculated: | 61.21 | 7.19 | 7.14 |
| Found: | 61.06 | 7.28 | 7.06 |

EXAMPLE 6

N-Ethyl-4-(3-hexahydrocyclopenta[c]pyrrol-2(1H)-ylpropoxy)-benzamide

The experimental procedure is identical to that of Example 1, with the replacement of 4-hydroxybenzonitrile in Step 1 with N-ethyl-4-hydroxybenzamide.

Elemental Microanalyses:

|  | C % | H % | N % |
|---|---|---|---|
| Calculated: | 72.12 | 8.92 | 8.85 |
| Found: | 72.52 | 9.10 | 8.80 |

EXAMPLE 7

N-Cyclopentyl-4-(3-hexahydrocyclopenta[c]pyrrol-2(1H)-ylpropoxy)-benzamide oxalate The experimental procedure is identical to that of Example 1, with the replacement of 4-hydroxybenzonitrile in Step 1 with N-cyclopentyl-4-hydroxybenzamide.

EXAMPLE 8

N-Cyclopentyl-N-ethyl-4-(3-hexahydrocyclopenta[c]pyrrol-2(1H)-ylpropoxy)benzamide oxalate The experimental procedure is identical to that of Example 1, with the replacement of 4-hydroxybenzonitrile in Step 1 with N-cyclopentyl-N-ethyl-4-hydroxybenzamide.

EXAMPLE 9

N,N-Diethyl-4-(3-hexahydrocyclopenta[c]pyrrol-2(1H)-ylpropoxy)-benzamide oxalate The experimental procedure is identical to that of Example 1, with the replacement of 4-hydroxybenzonitrile in Step 1 with N,N-diethyl-4-hydroxybenzamide.

Elemental Microanalyses:

|  | C % | H % | N % |
|---|---|---|---|
| Calculated: | 63.57 | 7.89 | 6.45 |
| Found: | 63.37 | 7.93 | 6.34 |

EXAMPLE 10

N,N-Dicyclopropyl-4-(3-hexahydrocyclopenta[c]pyrrol-2(1H)-ylpropoxy)benzamide oxalate The experimental procedure is identical to that of Example 1, with the replacement of 4-hydroxybenzonitrile in Step 1 with N,N-dicyclopropyl-4-hydroxybenzamide.

EXAMPLE 11

2-{3-[4-(1-Azepanylcarbonyl)phenoxy]propyl}octahydrocyclopenta-[c]pyrrole oxalate The experimental procedure is identical to that of Example 1, with the replacement of 4-hydroxybenzonitrile in Step 1 with 4-(1-azepanylcarbonyl)phenol.

EXAMPLE 12

2-{3-[4-(Thiomorpholinocarbonyl)phenoxy]propyl}octahydrocyclopenta[c]pyrrole oxalate The experimental procedure is identical to that of Example 1, with the replacement of 4-hydroxybenzonitrile in Step 1 with 4-(thiomorpholinocarbonyl)phenol.

EXAMPLE 13

2-{3-[4-(Morpholinocarbonyl)phenoxy]propyl}octahydrocyclopenta[c]pyrrole oxalate The experimental procedure is identical to that of Example 1, with the replacement of 4-hydroxybenzonitrile in Step 1 with 4-(morpholinocarbonyl)phenol.

Elemental Microanalyses:

|  | C % | H % | N % |
|---|---|---|---|
| Calculated: | 61.59 | 7.19 | 6.25 |
| Found: | 61.50 | 7.21 | 6.30 |

EXAMPLE 14

2-{3-[4-(1-piperazinylcarbonyl)phenoxy]propyl}octahydrocyclopenta[c]pyrrole oxalate The experimental procedure is identical to that of Example 1, with the replacement of 4-hydroxybenzonitrile in Step 1 with 4-(1-piperazinylcarbonyl)phenol.

EXAMPLE 15

2-[4-(3-Hexahydrocyclopenta[c]pyrrol-2(1H)-ylpropoxy)benzoyl]-isoindoline oxalate The experimental procedure is identical to that of Example 1, with the replacement of 4-hydroxybenzonitrile in Step 1 with 4-(1,3-dihydro-2H-isoindol-2-ylcarbonyl)phenol.

EXAMPLE 16

5-Bromo-2-[4-(3-hexahydrocyclopenta[c]pyrrol-2(1H)-ylpropoxy)-benzoyl]isoindoline oxalate The experimental procedure is identical to that of Example 1, with the replacement of 4-hydroxybenzonitrile in Step 1 with 4-[(5-bromo-1,3-dihydro-2H-isoindol-2-yl)carbonyl]-phenol.

EXAMPLE 17

2-{3-[4-(Hexahydrocyclopenta[c]pyrrol-2(1H)-ylcarbonyl)phenoxy]-propyl}octahydrocyclopenta[c]pyrrole oxalate The experimental procedure is identical to that of Example 1, with the replacement of 4-hydroxybenzonitrile in Step 1 with 4-(hexahydrocyclopenta[c]pyrrol-2(1H)-ylcarbonyl)-phenol.

Elemental Microanalyses:

|  | C % | H % | N % |
| --- | --- | --- | --- |
| Calculated: | 62.65 | 7.21 | 5.41 |
| Found: | 63.14 | 7.30 | 5.47 |

EXAMPLE 18

4-[(4-Hexahydrocyclopenta[c]pyrrol-2(1H)-ylbutyl)amino]-benzonitrile oxalate

Step 1: N-(4-Cyanophenyl)-N-(4-hexahydrocyclopenta[c]pyrrol-2(1H)-ylbutyl)-acetamide 2 g (8 mmol) of the chlorine compound synthesised in Preparation 1 are dissolved in 65 ml of ethanol with 1.5 g of octahydrocyclopenta[c]pyrrole (2 eq.) and 12 mg of NaI (0.01 eq.). The mixture is heated at reflux for 18 hours before being evaporated to dryness in vacuo. The residue is taken up in ethyl acetate and then washed with N sodium hydroxide solution. The organic phase is dried over magnesium sulphate, concentrated and purified by column chromatography on silica (eluant: dichloromethane/ethanol: 9/1) to yield 1.4 g of the expected product.

Step 2: 4-[(4-Hexahydrocyclopenta[c]pyrrol-2(1H)-ylbutyl)amino]benzonitrile oxalate 133 mg (1.5 eq.) of sodium ethanolate are added to a solution of the compound prepared in the above Step (423 mg) in 2.6 ml of ethanol. The mixture is heated at reflux for 5 hours and then concentrated in vacuo. The residue is taken up in dichloromethane, washed with water and then dried over magnesium sulphate before evaporation of the solvent. Purification by column chromatography (eluant: dichloromethane/ethanol/ammonium hydroxide: 10/0.5/0.25) allows 330 mg of product to be obtained. 260 mg of that compound are dissolved in ethanol and then the addition of 2.5 equivalents of oxalic acid in solution in ethanol results in precipitation of the salt.

ESI$^+$: [M+H]$^+$ 284.2085 (theory: 284.2127)

EXAMPLE 19

4-[(3-Hexahydrocyclopenta[c]pyrrol-2(1H)-ylpropyl)amino]benzonitrile oxalate The experimental procedure is identical to that of Example 18, with the replacement of the reagent of Preparation 1 with that of Preparation 2.

Elemental Microanalyses:

|  | C % | H % | N % |
| --- | --- | --- | --- |
| Calculated: | 63.49 | 7.01 | 11.69 |
| Found: | 63.22 | 7.04 | 11.47 |

EXAMPLE 20

4-[(2-Hexahydrocyclopenta[c]pyrrol-2(1H)-ylethyl)amino]benzonitrile oxalate

The experimental procedure is identical to that of Example 18, with the replacement of the reagent of Preparation 1 with that of Preparation 3.

Elemental Microanalyses:

|  | C % | H % | N % |
| --- | --- | --- | --- |
| Calculated: | 60.81 | 6.49 | 11.56 |
| Found: | 60.60 | 6.00 | 11.30 |

EXAMPLE 21

4-[(4-Hexahydrocyclopenta[c]pyrrol-2(1H)-ylbutyl)amino]-benzamide oxalate 436 mg of the compound of Example 18 are dissolved in 4 ml of ethanol. 86 mg of potassium hydroxide (1 eq.) are dissolved in 1.5 ml of water before being added to the alcohol solution. The mixture is heated at reflux for 1.5 hours and then evaporated to dryness. The residue is taken up in dichloromethane. The resulting solution is washed with water, dried over magnesium sulphate and then concentrated in vacuo. The product is crystallised in oxalate form.

ESI$^+$: [M+H]$^+$ 302.2212 (theory: 302.2232)

EXAMPLE 22

4-(3-Hexahydrocyclopenta[c]pyrrol-2(1H)-ylpropoxy)benzamide oxalate

The experimental procedure is identical to that of Example 21, using the compound of Example 1 as starting material.

Elemental Microanalyses:

|  | C % | H % | N % |
|---|---|---|---|
| Calculated: | 60.30 | 6.93 | 7.40 |
| Found: | 60.21 | 6.65 | 7.31 |

EXAMPLE 23

4-[(3-Hexahydroyclopenta[c]pyrrol-2(1H)-ylpropyl) amino]-benzamide oxalate

The experimental procedure is identical to that of Example 21, using the compound of Example 19 as starting material.

EXAMPLE 24

4-[(2-Hexahydrocyclopenta[c]pyrrol-2(1H)-ylethyl) amino]benzamide oxalate

The experimental procedure is identical to that of Example 21, using the compound of Example 20 as starting material.

EXAMPLE 25

N-{4-[3-(Hexahydrocyclopenta[c]pyrrol-2(1H)-yl) propoxy]phenyl}-2-methylpropanamide oxalate The experimental procedure is identical to that of Example 31, with the replacement of 4-fluorobenzoyl chloride in Step 2 with 2-methylpropanoyl chloride.

Elemental Microanalyses:

|  | C % | H % | N % |
|---|---|---|---|
| Calculated: | 61.20 | 7.66 | 6.45 |
| Found: | 61.32 | 7.47 | 6.24 |

EXAMPLE 26

N-{4-[3-(Hexahydrocyclopenta [c]pyrrol-2(1H)-yl) propoxy]phenyl}-2,2-dimethylpropanamide The experimental procedure is identical to that of Example 31, with the replacement of 4-fluorobenzoyl chloride in Step 2 with 2,2-dimethylpropanoyl chloride.

Elemental Microanalyses:

|  | C % | H % | N % |
|---|---|---|---|
| Calculated: | 73.22 | 9.36 | 8.13 |
| Found: | 73.69 | 9.33 | 8.20 |

EXAMPLE 27

N-{4-[3-(Hexahydrocyclopenta[c]pyrrol-2(1H)-yl) propoxy]phenyl}-cyclopropanecarboxamide The experimental procedure is identical to that of Example 31, with the replacement of 4-fluorobenzoyl chloride in Step 2 with cyclopropanecarbonyl chloride.

Elemental Microanalyses:

|  | C % | H % | N % |
|---|---|---|---|
| Calculated: | 73.14 | 8.59 | 8.53 |
| Found: | 72.04 | 8.67 | 8.31 |

EXAMPLE 28

N-{4-[3-(Hexahydrocyclopenta [c]pyrrol-2(1H)-yl) propoxy]phenyl}-cyclobutanecarboxamide The experimental procedure is identical to that of Example 31, with the replacement of 4-fluorobenzoyl chloride in Step 2 with cyclobutanecarbonyl chloride.

Elemental Microanalyses:

|  | C % | H % | N % |
|---|---|---|---|
| Calculated: | 73.65 | 8.83 | 8.18 |
| Found: | 73.24 | 8.68 | 8.12 |

EXAMPLE 29

N-{4-[3-(Hexahydrocyclopenta [c]pyrrol-2(1H)-yl) propoxy]phenyl}-cyclohexanecarboxamide The experimental procedure is identical to that of Example 31, with the replacement of 4-fluorobenzoyl chloride in Step 2 with cyclohexanecarbonyl chloride.

Elemental Microanalyses:

|  | C % | H % | N % |
|---|---|---|---|
| Calculated: | 74.56 | 9.25 | 7.56 |
| Found: | 74.20 | 9.38 | 7.40 |

EXAMPLE 30

N-{4-[3-(Hexahydrocyclopenta [c]pyrrol-2(1H)-yl) propoxy]phenyl)}-4-nitrobenzamide The experimental procedure is identical to that of Example 31, with the replacement of 4-fluorobenzoyl chloride in Step 2 with 4-nitrobenzoyl chloride.

Elemental Microanalyses:

|  | C % | H % | N % |
|---|---|---|---|
| Calculated: | 67.46 | 6.65 | 10.26 |
| Found: | 68.18 | 6.60 | 10.31 |

EXAMPLE 31

N-{4-[3-(-Hexahydrocyclopenta[c]pyrrol-2(1H)-yl) propoxy]phenyl}-4-fluorobenzamide

Step 1: 4-[3-(Hexahydrocyclopenta[c]pyrrol-2(1H)-yl)propoxy]aniline

The title compound is obtained by acid hydrolysis of 1.5 g of the compound of Example 4 by heating it at reflux in 6N hydrochloric acid. The mixture is then concentrated and rendered alkaline in 20 ml of water and 10 ml of 1N sodium hydroxide solution and subsequently extracted with dichloromethane. A white solid is obtained by concentration of the organic phase (1.08 g).

Step 2: N-{4-[3-(Hexahydrocyclopenta[c]pyrrol-2(1H)-yl)propoxy]phenyl}-4-fluorobenzamide 0.24 g (1 mM) of the compound synthesised in the above Step is dissolved in 2.5 ml of anhydrous tetrahydrofuran and then cooled in an ice bath. There are added dropwise, in succession, 0.21 ml (1.5 mM) of triethylamine and 0.26 g (1 mM) of 4-fluorobenzoyl chloride. The mixture is maintained in an ice bath, with stirring, and is then left at ambient temperature, with stirring, for 16 h. The solution is diluted with ethyl acetate and extracted with (6N) sodium hydroxide solution, washed with water and then dried over magnesium sulphate and concentrated. The title product can be obtained in oxalate form by recrystallisation from ethanol (see Step 2 of Example 18).

Elemental Microanalyses:

|  | C % | H % | N % |
|---|---|---|---|
| Calculated: | 72.23 | 7.12 | 7.32 |
| Found: | 72.26 | 7.10 | 7.34 |

EXAMPLE 32

N-{4-[3-(Hexahydrocyclopenta [c]pyrrol-2(1H)-yl) propoxy]phenyl}-2-fluorobenzamide

The experimental procedure is identical to that of Example 31, with the replacement of 4-fluorobenzoyl chloride in Step 2 with 2-fluorobenzoyl chloride.

Elemental Microanalyses:

|  | C % | H % | N % |
|---|---|---|---|
| Calculated: | 72.23 | 7.12 | 7.32 |
| Found: | 72.01 | 7.03 | 7.28 |

EXAMPLE 33

N-{4-[3-(Hexahydrocyclopenta[c]pyrrol-2(1H)-yl) propoxy]phenyl}-2,4-difluorobenzamide

The experimental procedure is identical to that of Example 31, with the replacement of 4-fluorobenzoyl chloride in Step 2 with 2,4-difluorobenzoyl chloride.

Elemental Microanalyses:

|  | C % | H % | N % |
|---|---|---|---|
| Calculated: | 68.98 | 6.54 | 7.00 |
| Found: | 69.02 | 6.72 | 6.99 |

EXAMPLE 34

N-{4-[3-(Hexahydrocyclopenta[c]pyrrol-2(1H)-yl) propoxy]phenyl}-4-trifluoromethylbenzamide

The experimental procedure is identical to that of Example 31, with the replacement of 4-fluorobenzoyl chloride in Step 2 with 4-trifluoromethylbenzoyl chloride.

Elemental Microanalyses:

|  | C % | H % | N % |
|---|---|---|---|
| Calculated: | 66.65 | 6.29 | 6.48 |
| Found: | 66.64 | 6.39 | 6.51 |

EXAMPLE 35

N-{4-[3-(Hexahydrocyclopenta [c]pyrrol-2(1H)-yl) propoxy]phenyl}-2-trifluoromethylbenzamide

The experimental procedure is identical to that of Example 31, with the replacement of 4-fluorobenzoyl chloride in Step 2 with 2-trifluoromethylbenzoyl chloride.

Elemental Microanalyses:

|  | C % | H % | N % |
|---|---|---|---|
| Calculated: | 66.65 | 6.29 | 6.48 |
| Found: | 66.36 | 6.34 | 6.36 |

EXAMPLE 36

N-{4-[3-(Hexahydrocyclopenta[c]pyrrol-2(1H)-yl) propoxy]phenyl}-4-methoxybenzamide oxalate

The experimental procedure is identical to that of Example 31, with the replacement of 4-fluorobenzoyl chloride in Step 2 with 4-methoxybenzoyl chloride.

Elemental Microanalyses:

|  | C % | H % | N % |
|---|---|---|---|
| Calculated: | 64.45 | 6.66 | 5.78 |
| Found: | 64.57 | 6.65 | 5.78 |

EXAMPLE 37

N-{4-[3-(Hexahydrocyclopenta[c]pyrrol-2(1H)-yl)
propoxy]phenyl}-2-naphthamide

The experimental procedure is identical to that of Example 31, with the replacement of 4-fluorobenzoyl chloride in Step 2 with 2-naphthoyl chloride.

Elemental Microanalyses:

|  | C % | H % | N % |
|---|---|---|---|
| Calculated: | 78.23 | 7.29 | 6.76 |
| Found: | 78.36 | 7.26 | 6.81 |

EXAMPLE 38

N-{4-[3-(Hexahydrocyclopenta [c]pyrrol-2(1H)-yl)
propoxy]phenyl)}-1-naphthamide oxalate The experimental procedure is identical to that of Example 31, with the replacement of 4-fluorobenzoyl chloride in Step 2 with 1-naphthoyl chloride.

Elemental Microanalyses:

|  | C % | H % | N % |
|---|---|---|---|
| Calculated: | 69.03 | 6.39 | 5.55 |
| Found: | 68.57 | 6.33 | 5.68 |

EXAMPLE 39

N-{4-[3-(Hexahydrocyclopenta[c]pyrrol-2(1H)-yl)
propoxy]phenyl}-2-furancarboxamide The experimental procedure is identical to that of Example 31, with the replacement of 4-fluorobenzoyl chloride in Step 2 with 2-furoyl chloride.

Elemental Microanalyses:

|  | C % | H % | N % |
|---|---|---|---|
| Calculated: | 71.16 | 7.39 | 7.90 |
| Found: | 70.90 | 7.44 | 7.87 |

EXAMPLE 40

N-{4-[3-(Hexahydrocyclopenta[c]pyrrol-2(1H)-yl)
propoxy]phenyl}-2-thiophenecarboxamide The experimental procedure is identical to that of Example 31, with the replacement of 4-fluorobenzoyl chloride in Step 2 with 2-thenoyl chloride.

Elemental Microanalyses:

|  | C % | H % | N % | S % |
|---|---|---|---|---|
| Calculated: | 68.08 | 7.07 | 7.56 | 8.65 |
| Found: | 68.21 | 7.09 | 7.50 | 8.52 |

EXAMPLE 41

N-{4-[3-(Hexahydrocyclopenta[c]pyrrol-2(1H)-yl)
propoxy]phenyl}-isonicotinamide

The experimental procedure is identical to that of Example 31, with the replacement of 4-fluorobenzoyl chloride in Step 2 with isonicotinoyl chloride.

Elemental Microanalyses:

|  | C % | H % | N % |
|---|---|---|---|
| Calculated: | 72.30 | 7.45 | 11.50 |
| Found: | 72.63 | 7.57 | 11.44 |

EXAMPLE 42

N-{4-[3-(Hexahydrocyclopenta[c]pyrrol-2(1H)-yl)
propoxy]phenyl}-benzo[b]thiophene-3-carboxamide The experimental procedure is identical to that of Example 31, with the replacement of 4-fluorobenzoyl chloride in Step 2 with benzo[b]thiophene-3-carbonyl chloride.

Elemental Microanalyses:

|  | C % | H % | N % | S % |
|---|---|---|---|---|
| Calculated: | 71.40 | 6.71 | 6.66 | 7.62 |
| Found: | 71.00 | 6.89 | 6.57 | 7.41 |

EXAMPLE 43

N-{(4-[3-(Hexahydrocyclopenta [c]pyrrol-2(1H)-yl)
propoxy]phenyl}-2-phenylacetamide The experimental procedure is identical to that of Example 31, with the replacement of 4-fluorobenzoyl chloride in Step 2 with phenylacetyl chloride.

Elemental Microanalyses:

|  | C % | H % | N % |
|---|---|---|---|
| Calculated: | 76.16 | 7.99 | 7.40 |
| Found: | 76.33 | 8.00 | 7.26 |

EXAMPLE 44

N-{4-[3-(Hexahydrocyclopenta[c]pyrrol-2(1H)-yl)
propoxy]phenyl}-2-(3,4-dimethoxyphenyl)acetamide
oxalate The experimental procedure is identical to that of Example 31, with the replacement of 4-fluorobenzoyl chloride in Step 2 with (3,4-dimethoxyphenyl)acetyl chloride.

Elemental Microanalyses:

|  | C % | H % | N % |
|---|---|---|---|
| Calculated: | 63.62 | 6.86 | 5.30 |
| Found: | 63.32 | 6.72 | 5.22 |

EXAMPLE 45

N-{4-[3-(Hexahydrocyclopenta[c]pyrrol-2(1H)-yl)
propoxy]phenyl}-2-(2-thienyl)acetamide The experimental procedure is identical to that of Example 31, with the replacement of 4-fluorobenzoyl chloride in Step 2 with (2-thienyl)acetyl chloride.

Elemental Microanalyses:

|  | C % | H % | N % | S % |
|---|---|---|---|---|
| Calculated: | 68.72 | 7.34 | 7.28 | 8.34 |
| Found: | 68.57 | 7.45 | 7.20 | 8.92 |

EXAMPLE 46

N-{4-[3-(Hexahydrocyclopenta[c]pyrrol-2(1H)-yl)
propoxy]phenyl}-2,2-diphenylacetamide oxalate The experimental procedure is identical to that of Example 31, with the replacement of 4-fluorobenzoyl chloride in Step 2 with diphenylacetyl chloride.

Elemental Microanalyses:

|  | C % | H % | N % |
|---|---|---|---|
| Calculated: | 70.57 | 6.66 | 5.14 |
| Found: | 70.15 | 6.72 | 5.18 |

EXAMPLE 47

N-{4-[3-(Hexahydrocyclopenta[c]pyrrol-2(1H)-yl)
propoxy]phenyl}-3-phenylpropanamide oxalate The experimental procedure is identical to that of Example 31, with the replacement of 4-fluorobenzoyl chloride in Step 2 with 3-phenylpropanoyl chloride.

Elemental Microanalyses:

|  | C % | H% | N % |
|---|---|---|---|
| Calculated: | 67.20 | 7.10 | 5.80 |
| Found: | 66.85 | 7.14 | 5.74 |

EXAMPLE 48

N-{4-[3-(Hexahydrocyclopenta [c]pyrrol-2(1H)-yl)
propoxy]phenyl}-2-methoxyacetamide oxalate The experimental procedure is identical to that of Example 31, with the replacement of 4-fluorobenzoyl chloride in Step 2 with methoxyacetyl chloride.

Elemental Microanalyses:

|  | C % | H % | N % |
|---|---|---|---|
| Calculated: | 56.96 | 6.98 | 6.09 |
| Found: | 57.28 | 6.77 | 6.05 |

EXAMPLE 49

N'-{4-[3-(Hexahydrocyclopenta[c]pyrrol-2(1H)-yl)
propoxy]phenyl}-N,N-dimethylurea The experimental procedure is identical to that of Example 31, with the replacement of 4-fluorobenzoyl chloride in Step 2 with dimethylcarbamoyl chloride.

Elemental Microanalyses:

|  | C % | H % | N % |
|---|---|---|---|
| Calculated: | 68.85 | 8.82 | 12.68 |
| Found: | 68.84 | 9.09 | 12.29 |

EXAMPLE 50

N-{4-[3-(Hexahydrocyclopenta[c]pyrrol-2(1H)-yl)
propoxy]phenyl}-morpholinocarboxamide The experimental procedure is identical to that of Example 31, with the replacement of 4-fluorobenzoyl chloride in Step 2 with morpholinocarbonyl chloride.

Elemental Microanalyses:

|  | C % | H % | N % |
|---|---|---|---|
| Calculated: | 67.53 | 8.37 | 11.25 |
| Found: | 67.67 | 8.67 | 11.41 |

EXAMPLE 51

4-[3-(Hexahydrocyclopenta[c]pyrrol-2(1H)-yl)propoxy]-N-phenylbenzamide

The experimental procedure is identical to that of Example 1, with the replacement of 4-hydroxybenzonitrile in Step 1 with 4-hydroxy-N-phenylbenzamide.

Elemental Microanalyses:

|  | C % | H % | N % |
|---|---|---|---|
| Calculated: | 75.79 | 7.74 | 7.69 |
| Found: | 75.46 | 7.82 | 7.60 |

EXAMPLE 52

4-[3-(Hexahydrocyclopenta[c]pyrrol-2(1H)-yl)propoxy]-N-(4-fluorophenyl)benzamide The experimental procedure is identical to that of Example 1, with the replacement of 4-hydroxybenzonitrile in Step 1 with N-(4-fluorophenyl)-4-hydroxybenzamide.

Elemental Microanalyses:

|  | C % | H % | N % |
|---|---|---|---|
| Calculated: | 72.23 | 7.12 | 7.32 |
| Found: | 71.85 | 7.23 | 7.31 |

EXAMPLE 53

4-[3-(Hexahydrocyclopenta[c]pyrrol-2(1H)-yl)propoxy]-N-(1,3-benzodioxol-5-yl)benzamide The experimental procedure is identical to that of Example 1, with the replacement of 4-hydroxybenzonitrile in Step 1 with N-(1,3-benzodioxol-5-yl)-4-hydroxybenzamide.

Elemental Microanalyses:

|  | C % | H % | N % |
|---|---|---|---|
| Calculated: | 70.57 | 6.91 | 6.86 |
| Found: | 70.46 | 7.06 | 7.08 |

EXAMPLE 54

4-[3-(Hexahydrocyclopenta[c]pyrrol-2(1H)-yl)propoxy]-N-cyclohexylbenzamide

The experimental procedure is identical to that of Example 1, with the replacement of 4-hydroxybenzonitrile in Step 1 with N-cyclohexyl-4-hydroxybenzamide.

Elemental Microanalyses:

|  | C % | H % | N % |
|---|---|---|---|
| Calculated: | 74.56 | 9.25 | 7.56 |
| Found: | 74.11 | 9.30 | 7.36 |

EXAMPLE 55

4-[3-(Hexahydrocyclopenta[c]pyrrol-2(1H)-yl)propoxy]-N-methyl-N-cyclohexylbenzamide oxalate The experimental procedure is identical to that of Example 1, with the replacement of 4-hydroxybenzonitrile in Step 1 with N-methyl-N-cyclohexyl-4-hydroxybenzamide.

Elemental Microanalyses:

|  | C % | H % | N % |
|---|---|---|---|
| Calculated: | 65.80 | 8.07 | 5.90 |
| Found: | 65.06 | 7.64 | 6.07 |

EXAMPLE 56

4-[3-(Hexahydrocyclopenta[c]pyrrol-2(1H)-yl)propoxy]-N,N-dicyclohexylbenzamide

The experimental procedure is identical to that of Example 1, with the replacement of 4-hydroxybenzonitrile in Step 1 with N,N-dicyclohexyl-4-hydroxybenzamide.

Elemental Microanalyses:

|  | C % | H % | N % |
|---|---|---|---|
| Calculated: | 75.95 | 9.80 | 6.19 |
| Found: | 76.23 | 9.86 | 6.11 |

EXAMPLE 57

2-[3-(4-Piperidinocarbonylphenoxy)propyl]octahydrocyclopenta[c]pyrrole oxalate

The experimental procedure is identical to that of Example 1, with the replacement of 4-hydroxybenzonitrile in Step 1 with 4-(1-piperidinocarbonyl)phenol.

Elemental Microanalyses:

|  | C % | H % | N % |
|---|---|---|---|
| Calculated: | 61.09 | 7.18 | 5.70 |
| Found: | 61.05 | 7.33 | 5.60 |

EXAMPLE 58

1-{4-[3-(Hexahydrocyclopenta[c]pyrrol-2(1H)-yl) propoxy]benzoyl}-1,2,3,4-tetrahydroquinoline dioxalate The experimental procedure is identical to that of Example 1, with the replacement of 4-hydroxybenzonitrile in Step 1 with 4-(3,4-dihydro-1(2H)-quinolylcarbonyl)phenol.

Elemental Microanalyses:

|  | C % | H % | N % |
|---|---|---|---|
| Calculated: | 63.33 | 6.40 | 5.72 |
| Found: | 63.47 | 6.61 | 5.16 |

EXAMPLE 59

2-[3-(4-[Piperidinopiperidinocarbonyl]phenoxy) propyl]octahydrocyclopenta[c]pyrrole dioxalate The experimental procedure is identical to that of Example 1, with the replacement of 4-hydroxybenzonitrile in Step 1 with 4-piperidinopiperidinocarbonylphenol.

Elemental Microanalyses:

|  | C % | H % | N % |
|---|---|---|---|
| Calculated: | 57.82 | 6.98 | 6.32 |
| Found: | 57.51 | 7.17 | 6.27 |

EXAMPLE 60

2-(3-{4-[(4-Methyl-1-piperazinyl)carbonyl] phenoxy}propyl)octahydrocyclopenta[c]pyrrole dioxalate The experimental procedure is identical to that of Example 1, with the replacement of 4-hydroxybenzonitrile in Step 1 with 4-[(4-methyl-1-piperazinyl)carbonyl]phenol.

Elemental Microanalyses:

|  | C % | H % | N % |
|---|---|---|---|
| Calculated: | 54.45 | 6.26 | 7.06 |
| Found: | 54.82 | 6.51 | 7.00 |

EXAMPLE 61

2-(3-{4-[(4-Benzyl-1-piperazinyl)carbonyl] phenoxy}propyl)octahydrocyclopenta[c]pyrrole dioxalate The experimental procedure is identical to that of Example 1, with the replacement of 4-hydroxybenzonitrile in Step 1 with 4-[(4-benzyl-1-piperazinyl)carbonyl]phenol.

Elemental Microanalyses:

|  | C % | H % | N % |
|---|---|---|---|
| Calculated: | 56.90 | 6.04 | 5.85 |
| Found: | 58.55 | 6.39 | 6.43 |

EXAMPLE 62

4-[3-(Hexahydrocyclopenta[c]pyrrol-2(1H)-yl)propoxy]-N-(1-benzylpiperidino)benzamide The experimental procedure is identical to that of Example 1, with the replacement of 4-hydroxybenzonitrile in Step 1 with N-(1-benzylpiperidino)-4-hydroxybenzamide.

Elemental Microanalyses:

|  | C % | H % | N % |
|---|---|---|---|
| Calculated: | 75.45 | 8.52 | 9.10 |
| Found: | 75.36 | 8.52 | 9.07 |

EXAMPLE 63

4-[3-(Hexahydrocyclopenta[c]pyrrol-2(1H)-yl)propoxy]-N-(cyclopropylmethyl)benzamide The experimental procedure is identical to that of Example 1, with the replacement of 4-hydroxybenzonitrile in Step 1 with N-(cyclopropylmethyl)-4-hydroxybenzamide.

Elemental Microanalyses:

|  | C % | H % | N % |
|---|---|---|---|
| Calculated: | 73.65 | 8.83 | 8.18 |
| Found: | 72.99 | 8.92 | 8.80 |

EXAMPLE 64

4-[3-(Hexahydrocyclopenta[c]pyrrol-2(1H)-yl)propoxy]-N-benzylbenzamide

The experimental procedure is identical to that of Example 1, with the replacement of 4-hydroxybenzonitrile in Step 1 with N-benzyl-4-hydroxybenzamide.

Elemental Microanalyses:

|  | C % | H % | N % |
|---|---|---|---|
| Calculated | 76.16 | 7.99 | 7.40 |
| Found: | 76.20 | 8.06 | 7.41 |

EXAMPLE 65

4-[3-(Hexahydrocyclopenta[c]pyrrol-2(1H)-yl)propoxy]-N-benzyl-N-methylbenzamide oxalate The experimental procedure is identical to that of Example 1, with the replacement of 4-hydroxybenzonitrile in Step 1 with N-benzyl-N-methyl-4-hydroxybenzamide.

Elemental Microanalyses:

|  | C % | H % | N % |
|---|---|---|---|
| Calculated: | 67.20 | 7.10 | 5.80 |
| Found: | 66.85 | 7.17 | 5.82 |

EXAMPLE 66

4-[3-(Hexahydrocyclopenta[c]pyrrol-2(1H)-yl)propoxy]-N-benzyl-N-(4-methoxyphenyl)benzamide oxalate The experimental procedure is identical to that of Example 1, with the replacement of 4-hydroxybenzonitrile in Step 1 with N-benzyl-N-(4-methoxyphenyl)-4-hydroxybenzamide.

Elemental Microanalyses:

|  | C % | H % | N % |
|---|---|---|---|
| Calculated: | 68.97 | 6.66 | 4.87 |
| Found: | 68.18 | 6.50 | 4.86 |

EXAMPLE 67

4-[3-(Hexahydrocyclopenta[c]pyrrol-2(1H)-yl)propoxy]-N-(4-methylbenzyl)benzamide The experimental procedure is identical to that of Example 1, with the replacement of 4-hydroxybenzonitrile in Step 1 with N-(4-methylbenzyl)-4-hydroxybenzamide.

Elemental Microanalyses:

|  | C % | H % | N % |
|---|---|---|---|
| Calculated: | 76.50 | 8.22 | 7.14 |
| Found: | 76.28 | 8.19 | 7.06 |

EXAMPLE 68

4-[3-(Hexahydrocyclopenta[c]pyrrol-2(1H)-yl)propoxy]-N-(3-methylbenzyl)benzamide The experimental procedure is identical to that of Example 1, with the replacement of 4-hydroxybenzonitrile in Step 1 with N-(3-methylbenzyl)-4-hydroxybenzamide.

Elemental Microanalyses:

|  | C % | H % | N % |
|---|---|---|---|
| Calculated: | 76.50 | 8.22 | 7.14 |
| Found: | 76.01 | 8.31 | 6.96 |

EXAMPLE 69

4-[3-(Hexahydrocyclopenta[c]pyrrol-2(1H)-yl)propoxy]-N-(2-methylbenzyl)benzamide The experimental procedure is identical to that of Example 1, with the replacement of 4-hydroxybenzonitrile in Step 1 with N-(2-methylbenzyl)-4-hydroxybenzamide.

Elemental Microanalyses:

|  | C % | H % | N % |
|---|---|---|---|
| Calculated: | 76.50 | 8.22 | 7.14 |
| Found: | 76.38 | 8.32 | 7.05 |

EXAMPLE 70

4-[3-(Hexahydrocyclopenta[c]pyrrol-2(1H)-yl)propoxy]-N-(4-trifluoromethylbenzyl)benzamide The experimental procedure is identical to that of Example 1, with the replacement of 4-hydroxybenzonitrile in Step 1 with N-(4-trifluoromethylbenzyl)-4-hydroxybenzamide.

Elemental Microanalyses:

|  | C % | H % | N % |
|---|---|---|---|
| Calculated: | 67.25 | 6.55 | 6.27 |
| Found: | 67.24 | 6.47 | 6.23 |

EXAMPLE 71

4-[3-(Hexahydrocyclopenta[c]pyrrol-2(1H)-yl)propoxy]-N-(3-trifluoromethylbenzyl)benzamide oxalate The experimental procedure is identical to that of Example 1, with the replacement of 4-hydroxybenzonitrile in Step 1 with N-(3-trifluoromethylbenzyl)-4-hydroxybenzamide.

Elemental Microanalyses:

|  | C % | H % | N % |
|---|---|---|---|
| Calculated: | 60.44 | 5.82 | 5.22 |
| Found: | 59.40 | 5.77 | 5.07 |

EXAMPLE 72

4-[3-(Hexahydrocyclopenta[c]pyrrol-2(1H)-yl)propoxy]-N-(4-pyridylmethyl)benzamide The experimental procedure is identical to that of Example 1, with the replacement of 4-hydroxybenzonitrile in Step 1 with N-(4-pyridylmethyl)-4-hydroxybenzamide.

Elemental Microanalyses:

|  | C % | H % | N % |
|---|---|---|---|
| Calculated: | 72.79 | 7.70 | 11.07 |
| Found: | 72.11 | 7.56 | 10.81 |

EXAMPLE 73

4-[3-(Hexahydrocyclopenta[c]pyrrol-2(1H)-yl)propoxy]-N-furfurylbenzamide

The experimental procedure is identical to that of Example 1, with the replacement of 4-hydroxybenzonitrile in Step 1 with N-furfuryl-4-hydroxybenzamide.

Elemental Microanalyses:

|  | C % | H % | N % |
|---|---|---|---|
| Calculated: | 71.71 | 7.66 | 7.60 |
| Found: | 70.68 | 7.77 | 7.56 |

EXAMPLE 74

4-[3-(Hexahydrocyclopenta[c]pyrrol-2(1H)-yl)propoxy]-N-[2-(2-thienyl)ethyl]benzamide The experimental procedure is identical to that of Example 1, with the replacement of 4-hydroxybenzonitrile in Step 1 with N-[2-(2-thienylmethyl)ethyl]-4-hydroxybenzamide.

Elemental Microanalyses:

|  | C % | H % | N % | S % |
|---|---|---|---|---|
| Calculated: | 69.31 | 7.59 | 7.03 | 8.05 |
| Found: | 69.28 | 7.63 | 6.89 | 8.01 |

EXAMPLE 75

4-[3-(Hexahydrocyclopenta[c]pyrrol-2(1H)-yl)propoxy]-N-(3,4-dimethoxyphenethyl)benzamide The experimental procedure is identical to that of Example 1, with the replacement of 4-hydroxybenzonitrile in Step 1 with N-(3,4-dimethoxyphenethyl)-4-hydroxybenzamide.

Elemental Microanalyses:

|  | C % | H % | N % |
|---|---|---|---|
| Calculated: | 71.65 | 8.02 | 6.19 |
| Found: | 71.80 | 8.09 | 6.16 |

EXAMPLE 76

4-[3-(Hexahydrocyclopenta[c]pyrrol-2(1H)-yl)propoxy]-N-(2-piperidinoethyl)benzamide The experimental procedure is identical to that of Example 1, with the replacement of 4-hydroxybenzonitrile in Step 1 with N-(2-piperidinoethyl)-4-hydroxybenzamide.

$^1$H NMR (DMSO $D_6$): δ (ppm): 1.20-1.75 (m,12H); 1.90 (quint,2H); 2.15 (m,2H); 2.30-2.50 (m,8H); 2.60 (m,4H); 3.55 (quad,2H); 4.05 (t,2H); 7.00 (d,2H); 7.80 (d,2H); 8.20 (t,1H).

EXAMPLE 77

4-[3-(Hexahydrocyclopenta[c]pyrrol-2(1H)-yl)propoxy]-N-(2-morpholinoethyl)benzamide The experimental procedure is identical to that of Example 1, with the replacement of 4-hydroxybenzonitrile in Step 1 with N-(2-morpholinoethyl)-4-hydroxybenzamide.

Elemental Microanalyses:

|  | C % | H % | N % |
|---|---|---|---|
| Calculated: | 68.80 | 8.79 | 10.46 |
| Found: | 68.62 | 8.84 | 10.34 |

EXAMPLE 78

4-[3-(Hexahydrocyclopenta[c]pyrrol-2(1H)-yl)propoxy]-N-[3-(1H-imidazol-1-yl)propyl]benzamide dioxalate The experimental procedure is identical to that of Example 1, with the replacement of 4-hydroxybenzonitrile in Step 1 with N-[3-(1H-imidazol-1-yl)propyl]-4-hydroxybenzamide.

Elemental Microanalyses:

|  | C % | H % | N % |
|---|---|---|---|
| Calculated: | 56.24 | 6.29 | 9.72 |
| Found: | 55.99 | 6.44 | 9.60 |

EXAMPLE 79

4-[3-(Hexahydrocyclopenta[c]pyrrol-2(1H)-yl)propoxy]-N-(2-phenoxyethyl)benzamide The experimental procedure is identical to that of Example 1, with the replacement of 4-hydroxybenzonitrile in Step 1 with N-(2-phenoxyethyl)-4-hydroxybenzamide.

Elemental Microanalyses:

|  | C % | H % | N % |
|---|---|---|---|
| Calculated: | 73.50 | 7.89 | 6.86 |
| Found: | 72.76 | 7.82 | 6.85 |

EXAMPLE 80

4-[3-(Hexahydrocyclopenta[c]pyrrol-2(1H)-yl)propoxy]-N-(2-methoxyethyl)benzamide oxalate The experimental procedure is identical to that of Example 1, with the replacement of 4-hydroxybenzonitrile in Step 1 with N-(2-methoxyethyl)-4-hydroxybenzamide.

Elemental Microanalyses:

|  | C % | H % | N % |
|---|---|---|---|
| Calculated: | 60.54 | 7.39 | 6.42 |
| Found: | 61.07 | 7.54 | 6.49 |

EXAMPLE 81

4-[3-(Hexahydrocyclopenta[c]pyrrol-2(1H)-yl)propoxy]-N-[2-methoxy-1-(methoxymethyl)ethyl]benzamide oxalate The experimental procedure is identical to that of Example 1, with the replacement of 4-hydroxybenzonitrile in Step 1 with N-[2-methoxy-1-(methoxymethyl)ethyl]-4-hydroxybenzamide.

Elemental Microanalyses:

|  | C % | H % | N % |
|---|---|---|---|
| Calculated: | 59.99 | 7.55 | 5.83 |
| Found: | 59.54 | 7.44 | 5.60 |

EXAMPLE 82

4-[3-(Hexahydrocyclopenta[c]pyrrol-2(1H)-yl)propoxy]-N-(tert-butoxy)benzamide

The experimental procedure is identical to that of Example 1, with the replacement of 4-hydroxybenzonitrile in Step 1 with N-(tert-butoxy)-4-hydroxybenzamide.

Elemental Microanalyses:

|  | C % | H % | N % |
|---|---|---|---|
| Calculated: | 69.97 | 8.95 | 7.77 |
| Found: | 70.05 | 9.00 | 7.69 |

EXAMPLE 83

4-[3-(Hexahydrocyclopenta[c]pyrrol-2(1H)-yl)propoxy]-N-(2-ethylbutyl)benzamide oxalate The experimental procedure is identical to that of Example 1, with the replacement of 4-hydroxybenzonitrile in Step 1 with N-(2-ethylbutyl)-4-hydroxybenzamide.

Elemental Microanalyses:

|  | C % | H % | N % |
|---|---|---|---|
| Calculated: | 64.91 | 8.28 | 6.06 |
| Found: | 64.93 | 8.38 | 6.00 |

EXAMPLE 84

4-[3-(Hexahydrocyclopenta[c]pyrrol-2(1H)-yl)propoxy]-N-isopropylbenzamide

The experimental procedure is identical to that of Example 1, with the replacement of 4-hydroxybenzonitrile in Step 1 with N-isopropyl-4-hydroxybenzamide.

Elemental Microanalyses:

|  | C % | H % | N % |
|---|---|---|---|
| Calculated: | 72.69 | 9.15 | 8.48 |
| Found: | 73.10 | 9.36 | 8.54 |

EXAMPLE 85

4-[3-(Hexahydrocyclopenta [c]pyrrol-2(1H)-yl)propoxy]-N-(tert-butyl)benzamide oxalate The experimental procedure is identical to that of Example 1, with the replacement of 4-hydroxybenzonitrile in Step 1 with N-(tert-butyl)-4-hydroxybenzamide.

Elemental Microanalyses:

|  | C % | H % | N % |
|---|---|---|---|
| Calculated: | 63.57 | 7.89 | 6.45 |
| Found: | 63.82 | 8.12 | 6.32 |

EXAMPLE 86

4-[3-(Hexahydrocyclopenta[c]pyrrol-2(1H)-yl)propoxy]-N-propylbenzamide oxalate

The experimental procedure is identical to that of Example 1, with the replacement of 4-hydroxybenzonitrile in Step 1 with N-propyl-4-hydroxybenzamide.

Elemental Microanalyses:

|  | C % | H % | N % |
|---|---|---|---|
| Calculated: | 62.84 | 7.67 | 6.66 |
| Found: | 63.24 | 8.09 | 6.58 |

EXAMPLE 87

4-[3-(Hexahydrocyclopenta[c]pyrrol-2(1H)-yl)propoxy]-N,N-dimethylbenzamide oxalate The experimental procedure is identical to that of Example 1, with the replacement of 4-hydroxybenzonitrile in Step 1 with N,N-dimethyl-4-hydroxybenzamide.

Elemental Microanalyses:

|  | C % | H % | N % |
|---|---|---|---|
| Calculated: | 58.53 | 6.92 | 6.20 |
| Found: | 58.51 | 6.99 | 6.09 |

EXAMPLE 88

4-[3-(Hexahydrocyclopenta[c]pyrrol-2(1H)-yl)propoxy]-N,N-dipropylbenzamide oxalate The experimental procedure is identical to that of Example 1, with the replacement of 4-hydroxybenzonitrile in Step 1 with N,N-dipropyl-4-hydroxybenzamide.

Elemental Microanalyses:

|  | C % | H % | N % |
|---|---|---|---|
| Calculated: | 64.91 | 8.28 | 6.06 |
| Found: | 64.73 | 8.39 | 5.94 |

EXAMPLE 89

4-[3-(Hexahydrocyclopenta[c]pyrrol-2(1H)-yl)propoxy]-N-ethyl-N-methylbenzamide oxalate The experimental procedure is identical to that of Example 1, with the replacement of 4-hydroxybenzonitrile in Step 1 with N-ethyl-N-methyl-4-hydroxybenzamide.

Elemental Microanalyses:

|  | C % | H % | N % |
|---|---|---|---|
| Calculated: | 59.34 | 7.15 | 6.02 |
| Found: | 59.26 | 7.16 | 5.91 |

EXAMPLE 90

4-[3-(Hexahydrocyclopenta[c]pyrrol-2(1H)-yl)propoxy]-N-propyl-N-methylbenzamide oxalate The experimental procedure is identical to that of Example 1, with the replacement of 4-hydroxybenzonitrile in Step 1 with N-propyl-N-methyl-4-hydroxybenzamide.

Elemental Microanalyses:

|  | C % | H % | N % |
|---|---|---|---|
| Calculated: | 63.57 | 7.89 | 6.45 |
| Found: | 63.62 | 8.11 | 6.38 |

EXAMPLE 91

4-[3-(Hexahydrocyclopenta[c]pyrrol-2(1H)-yl)propoxy]-N-isopropyl-N-methylbenzamide oxalate The experimental procedure is identical to that of Example 1, with the replacement of 4-hydroxybenzonitrile in Step 1 with N-isopropyl-N-methyl-4-hydroxybenzamide.

Elemental Microanalyses:

|  | C % | H % | N % |
|---|---|---|---|
| Calculated: | 63.57 | 7.89 | 6.45 |
| Found: | 63.95 | 8.30 | 6.37 |

EXAMPLE 92

4-[3-(Hexahydrocyclopenta[c]pyrrol-2(1H)-yl)propoxy]-N-(tert-butyl)-N-methylbenzamide oxalate The experimental procedure is identical to that of Example 1, with the replacement of 4-hydroxybenzonitrile in Step 1 with N-(tert-butyl)-N-methyl-4-hydroxybenzamide.

Elemental Microanalyses:

|  | C % | H % | N % |
|---|---|---|---|
| Calculated: | 64.26 | 8.09 | 6.25 |
| Found: | 63.81 | 8.10 | 6.20 |

EXAMPLE 93

4-[3-(Hexahydrocyclopenta[c]pyrrol-2(1H)-yl)propoxy]-N-methylbenzamide

The experimental procedure is identical to that of Example 1, with the replacement of 4-hydroxybenzonitrile in Step 1 with N-methyl-4-hydroxybenzamide.

Elemental Microanalyses:

|  | C % | H % | N % |
|---|---|---|---|
| Calculated: | 71.49 | 8.67 | 9.26 |
| Found: | 71.35 | 8.85 | 9.18 |

EXAMPLE 94

4-[3-(Hexahydrocyclopenta[c]pyrrol-2(1H)-yl)propoxy]-3-bromobenzamide oxalate The experimental procedure is identical to that of Example 1, with the replacement of 4-hydroxybenzonitrile in Step 1 with 4-hydroxy-3-bromobenzamide.

ESI$^+$: [M+H]$^+$ 367.1031 (theory: 367.1021)

EXAMPLE 95

2-{3-[4-(1H-imidazol-1-yl)phenoxy]propyl}octahydrocyclopenta[c]-pyrrole dioxalate The experimental procedure is identical to that of Example 1, with the replacement of 4-hydroxybenzonitrile in Step 1 with 4-(1H-imidazol-1-yl)phenol.

Elemental Microanalyses:

|  | C % | H % | N % |
|---|---|---|---|
| Calculated: | 55.68 | 5.88 | 8.40 |
| Found: | 55.81 | 5.57 | 8.51 |

EXAMPLE 96

2-{3-[4-(1H-1,2,4-triazol-1-yl)phenoxy]propyl}octahydrocyclopenta[c]pyrrole oxalate The experimental procedure is identical to that of Example 1, with the replacement of 4-hydroxybenzonitrile in Step 1 with 4-(1H-1,2,4-triazol-1-yl)phenol.

Elemental Microanalyses:

|  | C % | H % | N % |
|---|---|---|---|
| Calculated: | 59.69 | 6.51 | 13.92 |
| Found: | 58.83 | 6.39 | 13.35 |

EXAMPLE 97

N-[4-(3-Hexahydrocyclopenta[c]pyrrol-2(1H)-ylpropoxy)phenyl]-N-(2-pyrimidinyl)amine oxalate The experimental procedure is identical to that of Example 1, with the replacement of 4-hydroxybenzonitrile in Step 1 with 4-(2-pyrimidinylamino)phenol.

Elemental Microanalyses:

|  | C % | H % | N % |
|---|---|---|---|
| Calculated: | 59.92 | 6.37 | 12.42 |
| Found: | 59.43 | 6.47 | 11.67 |

EXAMPLE 98

N-[4-(3-Hexahydrocyclopenta[c]pyrrol-2(1H)-ylpropoxy)phenyl]-2-quinolylamine dioxalate The experimental procedure is identical to that of Example 1, with the replacement of 4-hydroxybenzonitrile in Step 1 with 4-(2-quinolylamino)phenol.

Elemental Microanalyses:

|  | C % | H % | N % |
|---|---|---|---|
| Calculated: | 61.37 | 5.86 | 7.40 |
| Found: | 61.49 | 6.02 | 7.32 |

EXAMPLE 99

N-[4-(3-Hexahydrocyclopenta[c]pyrrol-2(1H)-ylpropoxy)phenyl]-1-isoquinolylamine The experimental procedure is identical to that of Example 1, with the replacement of 4-hydroxybenzonitrile in Step 1 with 4-(1-isoquinolylamino)phenol.

Elemental Microanalyses:

|  | C % | H % | N % |
|---|---|---|---|
| Calculated: | 77.49 | 7.54 | 10.84 |
| Found: | 76.81 | 7.68 | 10.68 |

EXAMPLE 100

N-[4-(3-Hexahydrocyclopenta[c]pyrrol-2(1H)-ylpropoxy)phenyl]-9H-purin-6-ylamine The experimental procedure is identical to that of Example 1, with the replacement of 4-hydroxybenzonitrile in Step 1 with 4-(9H-purin-6-ylamino)phenol.

Elemental Microanalyses:

|  | C % | H % | N % |
|---|---|---|---|
| Calculated: | 66.64 | 6.92 | 22.20 |
| Found: | 66.84 | 7.03 | 21.81 |

EXAMPLE 101

4-(3-Octahydro-2(1H)-isoquinolylpropoxy)benzonitrile oxalate

The experimental procedure is identical to that of Example 1, with the replacement of octahydrocyclopenta[c]pyrrole in Step 2 with decahydroisoquinoline. The decahydroisoquinoline was synthesised according to the method of Wiktop. B (*J. Am. Chem. Soc.,* 1948, 70, 2617).

Elemental Microanalyses:

|  | C % | H % | N % |
|---|---|---|---|
| Calculated: | 64.93 | 7.27 | 7.21 |
| Found: | 63.93 | 7.03 | 7.01 |

EXAMPLE 102

4-(3-Octahydro-2H-isoindol-2-ylpropoxy)benzonitrile oxalate

The experimental procedure is identical to that of Example 1, with the replacement of octahydrocyclopenta[c]pyrrole in Step 2 with octahydroisoindole. The octahydroisoindole was synthesised according to the method of Matsuki et al. (*Chem. Pharm. Bull.*, 1994, 42(1), 9-18).

Elemental Microanalyses:

|  | C % | H % | N % |
|---|---|---|---|
| Calculated: | 64.15 | 7.00 | 7.48 |
| Found: | 63.86 | 6.89 | 7.55 |

EXAMPLE 103

4-(4-Octahydro-2(1H)-isoquinolylbutoxy)benzonitrile oxalate

The experimental procedure is identical to that of Example 3, with the replacement of octahydrocyclopenta[c]pyrrole in Step 2 with decahydroisoquinoline.

Elemental Microanalyses:

|  | C % | H % | N % |
|---|---|---|---|
| Calculated: | 68.98 | 7.29 | 6.66 |
| Found: | 64.54 | 7.25 | 6.73 |

EXAMPLE 104

4-(3-Octahydro-2H-isoindol-2-ylpropoxy)benzamide

Step 1: 4-(3-Octahydro-2H-isoindol-2-ylpropoxy)benzonitrile

The experimental procedure is identical to that of Example 1, with the replacement of octahydrocyclopenta[c]pyrrole in Step 2 with octahydroisoindole.

Step 2: 4-(3-Octahydro-2H-isoindol-2-ylpropoxy)benzamide

The experimental procedure is identical to that of Example 21, with the replacement of the compound of Example 18 with the compound of the above Step.
ESI$^+$: [M+H]$^+$ 303.2072 (theory: 303.2073)

EXAMPLE 105

N-Methyl-4-(3-octahydro-2H-isoindol-2-ylpropoxy)benzamide

The experimental procedure is identical to that of Example 1, with the replacement of 4-hydroxybenzonitrile with N-methyl-4-hydroxybenzamide in Step 1, and octahydrocyclopenta[c]pyrrole with octahydroisoindole in Step 2.
ESI$^+$: [M+H]$^+$ 317.2240 (theory: 317.2229)

EXAMPLE 106

N,N-Dimethyl-4-(3-octahydro-2H-isoindol-2-ylpropoxy)benzamide

The experimental procedure is identical to that of Example 1, with the replacement of 4-hydroxybenzonitrile with N,N-dimethyl-4-hydroxybenzamide in Step 1, and octahydrocyclopenta[c]pyrrole with octahydroisoindole in Step 2.

Elemental Microanalyses:

|  | C % | H % | N % |
|---|---|---|---|
| Calculated: | 72.69 | 9.15 | 8.48 |
| Found: | 72.25 | 9.21 | 8.37 |

Pharmacological Studies of the Compounds of the Invention

EXAMPLE A

Cerebral Doses of N$^t$-Methylhistamine in the NMRI Mouse

The aim of this study, carried out according to the method of Taylor et al. (*Biochem. Pharm.*, 1992, 44, 1261-1267), is to evaluate the ex vivo activity of the compounds of the present invention as type H3 central histaminergic receptor antagonists. That activity is revealed by measuring central levels of N$^t$-methylhistamine, the principal metabolite of histamine, after oral administration of the compounds being studied. An increase in the cerebral concentrations of N$^t$-methylhistamine signifies an increase in histamine turnover by blockade of the type H3 central histaminergic receptors.

NMRI mice (18-20 g) are treated via oral administration with the compounds of the present invention or with their carrier (20 ml/kg). Two hours after the pharmacological treatment, the animals are sacrificed, the brains are removed, frozen in liquid nitrogen, weighed and homogenised in 0.1N HClO$_4$ at 4° C. The homogenates are centrifuged (15000 g, 17 min, 4° C.). The supernatants are recovered and divided into aliquots. The aliquots are frozen in liquid nitrogen and stored at −80° C. until their analysis.

Determination of the cerebral levels of N$^t$-methylhistamine is effected by capillary electrophoresis coupled with detection by laser-induced fluorescence (*J. Chromatogr. A.*, 1996, 755, 99-115). The tissue levels of N$^t$-methylhistamine are expressed in ng/g of fresh brain. Comparison between the cerebral levels of N$^t$-methylhistamine of the animals treated with the carrier (control) and the animals treated with the compounds of the present invention (n=5/group) is effected by single factor variance analysis followed, if necessary, by a supplementary analysis (Dunnett's test).

The results show that, at doses of from 3 to 10 mg/kg p.o., the compounds of the present invention are capable of increasing the endogenous cerebral concentrations of N$^t$-methylhistamine by more than 50%. By way of example, at doses of 3 mg/kg p.o., the compounds of Examples 4, 22 and 93 increase the endogenous cerebral concentrations of N$^t$-methylhistamine by 52%, 33% and 90%, respectively, and, at a dose of 10 mg/kg p.o., the compounds of Examples 1 and 22 increase the endogenous cerebral concentrations of N$^t$-methylhistamine by 92% and 85%, respectively. These results demonstrate that the compounds of the present invention are potent activators of the central histaminergic systems and are active via the oral route with a duration of action of at least several hours.

EXAMPLE B

Pharmaceutical Compositions

Formulation for the preparation of 1000 tablets each containing a dose of 100 mg:
compound of Example 22 . . . 100 g
hydroxypropyl cellulose . . . 20 g
polyvinylpyrrolidone . . . 20 g
wheat starch . . . 150 g
lactose . . . 900 g
magnesium stearate . . . 30 g

The invention claimed is:
1. A compound selected from those of formula (I):

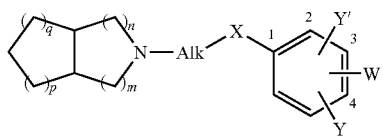

wherein:
m and n each represent 1,
p and q each represent 1,
Alk represents an alkylene, alkenylene or alkynylene chain,
Y and Y', which may be identical or different, each represent a hydrogen atom, a halogen atom or an alkyl, alkoxy, alkylthio, alkylsulphinyl, alkylsuiphonyl, mercapto, hydroxy, perhaloalkyl, nitro, amino unsubstituted or substituted by one or two alkyl groups, acyl, aminocarbonyl optionally substituted on the nitrogen atom by one or two alkyl groups, acylamino optionally substituted on the nitrogen atom by an alkyl group, alkoxycarbonyl, carboxy, sulpho or cyano group,
X represents an oxygen atom, a sulphur atom or an —N(R)— group wherein R represents a hydrogen atom or an alkyl group,
W represents a group selected from cyano, when X represents an oxygen atom or an NR group, —N($R_1$)-$Z_1$-$R_2$ and -$Z_2$-N$R_1R_2$,
wherein:
$Z_1$ represents —C(O)—, —C(S)—, —C(N$R_4$)—, *—C(O)—N($R_3$)—, *—C(S)—N($R_3$)—, *—C(N$R_4$)—N($R_3$)—, *—C(O)—O—, *—C(S)—O— or —S(O)$_r$—, wherein r represents 1 or 2, and * corresponds to the attachment to N($R_1$),
$Z_2$ represents —C(O)—, —C(S)—, —C(N$R_4$)—, —S(O)$_r$— or a bond,
$R_1$, $R_2$, $R_3$ and $R_4$, which may be identical or different, each represent a hydrogen atom, an optionally substituted alkyl group, optionally substituted alkenyl group, optionally substituted alkynyl group, alkoxy group, optionally substituted cycloalkyl group, or optionally substituted aryl group,
its enantiomers, diastereoisomers, and addition salts thereof with one or more pharmaceutically acceptable acid or base, it being understood that:

alkyl means a linear or branched hydrocarbon chain having from 1 to 6 carbon atoms,
alkenyl means a linear or branched group having from 3 to 6 carbon atoms and from 1 to 3 double bonds,
alkynyl means a linear or branched group having from 3 to 6 carbon atoms and from 1 to 3 triple bonds,
alkoxy means an alkyl-oxy group in which the linear or branched alkyl chain has from 1 to 6 carbon atoms,
optionally substituted aryloxy means a group of which the aryl group is optionally substituted,
acyl means an $R_aC(O)$— group in which $R_a$ represents a hydrogen atom or an alkyl group,
perhaloalkyl means a linear or branched carbon chain having from 1 to 3 carbon atoms and from 1 to 7 halogen atoms,
alkylene means a linear or branched bivalent radical having from 1 to 6 carbon atoms,
alkenylene means a linear or branched bivalent radical having from 2 to 6 carbon atoms and from 1 to 3 double bonds,
alkynylene means a linear or branched bivalent radical having from 2 to 6 carbon atoms and from 1 to 3 triple bonds,
aryl means a phenyl, naphthyl, indanyl, indenyl, dihydronaphthyl or tetrahydronaphthyl group,
cycloalkyl means a hydrocarbon monocycle or bicycle having from 3 to 11 carbon atoms and optionally unsaturated by 1 or 2 unsaturated bonds,
optionally substituted as applied to the terms cycloalkyl, and aryl means i) the group may be substituted by 1 to 3 identical or different substituents selected from alkyl, alkoxy, alkylthio, alkylsulphinyl, alkylsulphonyl, halogen, hydroxy, mercapto, perhaloalkyl, nitro, amino unsubstituted or substituted by one or two alkyl groups, acyl, aminocarbonyl optionally substituted on the nitrogen atom by one or two alkyl groups, acylamino optionally substituted on the nitrogen atom by an alkyl group, alkoxycarbonyl, carboxy, sulpho and cyano; or ii) the group may be substituted by an aryl, cycloalkyl, or benzyl group ; it being understood that the aryl group may in addition be substituted by one or two oxo groups on the non-aromatic moiety of a group having both non aromatic and aromatic moieties and that the cycloalkyl group may likewise be substituted by one or two oxo groups,
optionally substituted as applied to the term alkyl, alkenyl or alkynyl means the group may be substituted by one or two identical or different groups selected from alkylthio, alkylsulphinyl, alkylsulphonyl, alkoxy, halogen, hydroxy, mercapto, nitro, amino, acyl, aminocarbonyl, acylamino, alkoxycarbonyl, carboxy, sulpho, cyano, optionally substituted aryl, optionally substituted cycloalkyl, and optionally substituted aryloxy.

2. The compound of claim 1, wherein q is 1, its enantiomers, diastereoisomers, and addition salts thereof with one or more pharmaceutically acceptable acid or base.

3. The compound of claim 1, wherein n is 1, its enantiomers, diastereoisomers, and addition salts thereof with one or more pharmaceutically acceptable acid or base.

4. The compound of claim 1, wherein m is 1, its enantiomers, diastereoisomers, and addition salts thereof with one or more pharmaceutically acceptable acid or base.

5. The compound of claim 1, wherein p is 1, its enantiomers, diastereoisomers, and addition salts thereof with one or more pharmaceutically acceptable acid or base.

6. The compound of claim 1, wherein X represents an oxygen atom or a sulphur atom, its enantiomers, diastereoisomers, and addition salts thereof with one or more pharmaceutically acceptable acid or base.

7. The compound of claim 1, wherein X represents an —N(R)— group, its enantiomers, diastereoisomers, and addition salts thereof with one or more pharmaceutically acceptable acid or base.

8. The compound of claim 1, wherein Y and Y' represent a hydrogen atom, its enantiomers, diastereoisomers, and addition salts thereof with one or more pharmaceutically acceptable acid or base.

9. The compound of claim 1, wherein Y represents a hydrogen atom and Y' represents a halogen atom or an alkyl, alkoxy, alkylthio, alkylsulphinyl, alkylsulphonyl, mercapto, hydroxy, perhaloalkyl, nitro, amino unsubstituted or substituted by one or two alkyl groups, acyl, aminocarbonyl optionally substituted on the nitrogen atom by one or two alkyl groups, acylamino optionally substituted on the nitrogen atom by an alkyl group, alkoxycarbonyl, carboxy, sulpho or cyano group, its enantiomers, diastereoisomers, and addition salts thereof with one or more pharmaceutically acceptable acid or base.

10. The compound of claim 1, wherein Alk represents an alkylene chain, its enantiomers, diastereoisomers, and addition salts thereof with one or more pharmaceutically acceptable acid or base.

11. The compound of claim 1, wherein W is located on the phenyl group in the 4-position, its enantiomers, diastereoisomers, and addition salts thereof with one or more pharmaceutically acceptable acid or base.

12. The compound of claim 1, wherein W represents a cyano group, its enantiomers, diastereoisomers, and addition salts thereof with one or more pharmaceutically acceptable acid or base.

13. The compound of claim 1, wherein W represents an —N($R_1$)-$Z_1$-$R_2$ group, its enantiomers, diastereoisomers, and addition salts thereof with one or more pharmaceutically acceptable acid or base.

14. The compound of claim 1, wherein W represents a -$Z_2$-N$R_1R_2$ group, its enantiomers, diastereoisomers, and addition salts thereof with one or more pharmaceutically acceptable acid or base.

15. The compound of claim 1, wherein $Z_2$ represents a group selected from —C(O)—, —C(S)—, —C(N$R_4$)— and —S(O)$_r$—, its enantiomers, diastereoisomers, and addition salts thereof with one or more pharmaceutically acceptable acid or base.

16. The compound of claim 1, wherein $Z_2$ represents a bond, its enantiomers, diastereoisomers, and addition salts thereof with one or more pharmaceutically acceptable acid or base.

17. The compound of claim 1, wherein $Z_1$ represents a group selected from —C(O)—, —C(S)—, *—C(O)—N($R_3$)—, *—C(S)—N($R_3$)—, *—C(O)—O— and —S(O)$_2$—, its enantiomers, diastereoisomers, and addition salts thereof with one or more pharmaceutically acceptable acid or base.

18. The compound of claim 1, wherein $R_1$, $R_2$, $R_3$ and $R_4$, which may be identical or different, each represent a hydrogen atom or a group selected from cycloalkyl; alkoxy; optionally substituted phenyl; naphthyl; and an alkyl group optionally substituted by
an optionally substituted phenyl group,
a cycloalkyl group,
one or two alkoxy groups, or
a phenyloxy group its enantiomers, diastereoisomers, and addition salts thereof with one or more pharmaceutically acceptable acid or base.

19. The compound of claim 1, wherein W represents a -$Z_2$-N$R_1R_2$ group in which $Z_2$ represents a bond;
$R_1$ represents a hydrogen atom or an alkyl group and $R_2$ represents an aryl group, its enantiomers, diastereoisomers, and addition salts thereof with one or more pharmaceutically acceptable acid or base.

20. The compound of claim 1, wherein W represents a —C(O)—N$R_1R_2$ group in which $R_1$ and $R_2$, independently, each represent an alkyl group or a hydrogen atom, its enantiomers, diastereoisomers, and addition salts thereof with one or more pharmaceutically acceptable acid or base.

21. The compound of claim 1, wherein W represents a —C(O)—N$R_1R_2$ group in which $R_1$ and $R_2$, independently, each represent an alkyl group or a hydrogen atom, its enantiomers, diastereoisomers, and addition salts thereof with one or more pharmaceutically acceptable acid or base.

22. The compound of claim 1, wherein W represents a —N($R_1$)—C(O)—$R_2$ group in which $R_1$ and $R_2$, independently, each represent an alkyl group or a hydrogen atom, its enantiomers, diastereoisomers, and addition salts thereof with one or more pharmaceutically acceptable acid or base.

23. The compound of claim 1, which is 4-(3-hexahydrocyclopenta[c]pyrrol-2(1H)-ylpropoxy)benzonitrile, its enantiomers, diastereo-isomers, and addition salts thereof with one or more pharmaceutically acceptable acid.

24. The compound of claim 1, which is 4-(3-hexahydrocyclopenta[c]-pyrrol-2(1H)-ylpropoxy)benzamide, its enantiomers, diastereo-isomers, and addition salts thereof with one or more pharmaceutically acceptable acid.

25. The compound of claim 1, which is 4-[3-(hexahydrocyclopenta[c]pyrrol-2(1H)-yl)propoxy]-N-methyl-benzamide, its enantiomers, diastereoisomers, and addition salts thereof with one or more pharmaceutically acceptable acid.

26. The compound of claim 1, which is 4-[3-(hexahydrocyclopenta[c]pyrrol-2(1H)-yl)propoxy]-N,N-dimethyl-benzamide, its enantiomers, diastereoisomers, and addition salts thereof with one or more pharmaceutically acceptable acid.

27. The compound of claim 1, which is N-[4-(3-hexahydrocyclopenta[c]pyrrol-2(1H)-ylpropoxy)phenyl]acetamide its enantiomers, diastereoisomers, and addition salts thereof with one or more pharmaceutically acceptable acid.

28. A pharmaceutical composition comprising as active ingredient a compound of claim 1, alone or in combination with one or more pharmaceutically acceptable, inert, non-toxic excipients or carriers.

29. A method for treating a living animal body, including a human, afflicted with a condition selected from mood disorders, convulsive attacks, attention deficit hyperactivity syndrome, obesity, pain, and cognitive deficiencies associated with cerebral ageing and with neurodegenerative diseases comprising the step of administering to the living animal body, including a human, an amount of the compound of claim 1 which is effective for alleviation of the condition.

30. A method for treating a living animal body, including a human, afflicted with a condition selected from cognitive deficiencies associated with Alzheimer's disease, Parkinson's disease, Pick's disease, Korsakoff's disease, and frontal and sub-cortical dementias of vascular or other origins comprising the step of administering to the living animal body, including a human, an amount of the compound of claim 1 which is effective for alleviation of the condition.

* * * * *

UNITED STATES PATENT AND TRADEMARK OFFICE
CERTIFICATE OF CORRECTION

| | | |
|---|---|---|
| PATENT NO. | : 7,576,120 B2 | Page 1 of 1 |
| APPLICATION NO. | : 10/589831 | |
| DATED | : August 18, 2009 | |
| INVENTOR(S) | : Patrick Casara et al. | |

It is certified that error appears in the above-identified patent and that said Letters Patent is hereby corrected as shown below:

Title Page, Item (22) PCT Filing Date: "Feb. 20, 2005" should be --Feb. 18, 2005--.

Title Page, Item (56) References Cited: "5,703,091" should be --5,073,091--.

Signed and Sealed this
Eighth Day of March, 2011

David J. Kappos
*Director of the United States Patent and Trademark Office*